US010743940B2

(12) United States Patent
Zeilhofer et al.

(10) Patent No.: US 10,743,940 B2
(45) Date of Patent: Aug. 18, 2020

(54) NAVIGATION SYSTEM AND METHOD FOR DENTAL AND CRANIO-MAXILLOFACIAL SURGERY, POSITIONING TOOL AND METHOD OF POSITIONING A MARKER MEMBER (71) Applicant: Mininavident AG, Basel (CH)

(72) Inventors: Hans-Florian Zeilhofer, Basel (CH); Philipp Jürgens, Weil am Rehin (DE); Erik Schkommodau, Liestal (CH); Frank Berlinghoff, Munich (DE)

(73) Assignee: Mininavident AG, Basel (CH)

( * ) Notice: Subject to any disclaimer, the term of this patent is extended or adjusted under 35 U.S.C. 154(b) by 0 days.

(21) Appl. No.: 15/026,789

(22) PCT Filed: Oct. 2, 2013

(86) PCT No.: PCT/EP2013/070553
§ 371 (c)(1),
(2) Date: Apr. 1, 2016

(87) PCT Pub. No.: WO2015/048994
PCT Pub. Date: Apr. 9, 2015

(65) Prior Publication Data
US 2016/0235483 A1 Aug. 18, 2016

(51) Int. Cl.
A61B 34/20 (2016.01)
A61C 1/08 (2006.01)
(Continued)

(52) U.S. Cl.
CPC .......... A61B 34/20 (2016.02); A61B 1/00045 (2013.01); A61B 1/24 (2013.01);
(Continued)

(58) Field of Classification Search
CPC .......... A61C 1/082; A61C 1/084; A61C 1/12; A61C 8/0089; A61C 3/02; A61C 9/0046;
(Continued)

(56) References Cited

U.S. PATENT DOCUMENTS 4,824,367 A * 4/1989 Rosenstiel ............. A61C 1/082
433/27
5,049,070 A * 9/1991 Ademovic ............. A61B 1/042
348/66

(Continued)

FOREIGN PATENT DOCUMENTS

DE 20 2011 005573 U1 4/2012
EP 1 563 799 A1 8/2005
(Continued)

OTHER PUBLICATIONS

International Search Report and Written Opinion for Application No. PCT/EP2013/070553, dated Jun. 17, 2014.
(Continued)

Primary Examiner — Sean M Michalski
Assistant Examiner — Shannel N Wright
(74) Attorney, Agent, or Firm — Wolf, Greenfield & Sacks, P.C.

(57) ABSTRACT

The invention relates to a navigation system for dental and cranio-maxillofacial surgery, comprising a surgical handpiece (2), an imaging unit (4) which is movably attached to the surgical handpiece (2), and a marker member (6; 44, 46) which is attachable to a cranial bone, a facial bone (26), a tooth or teeth of a patient. The marker member (6; 44, 46) comprises a plurality of marker elements (8, 10; 46) which are detectable by the imaging unit (4). Further, the invention relates to a positioning tool (40) for use with the navigation system, wherein the positioning tool (40) is configured for positioning the marker member (44, 46) on a patient's
(Continued)

cranial bone, facial bone (26), tooth or teeth and comprises a die element (42) and the marker member (44, 46). The marker member (44, 46) comprises a deformable material (44), the deformable material (44) is releasably received in the die element (42) and the plurality of marker elements (46) are arranged on a surface of the deformable material (44) which faces the die element (42), The invention further relates to a navigation method for dental and craniomaxillofacial surgery using the navigation system and to a method of positioning a marker member (44, 46) on a patient's cranial bone, facial bone (26), tooth or teeth using the positioning tool (40).

20 Claims, 2 Drawing Sheets (51) Int. Cl.
| | | |
|---|---|---|
| A61C 9/00 | (2006.01) | |
| A61C 1/12 | (2006.01) | |
| A61C 3/02 | (2006.01) | |
| A61B 34/10 | (2016.01) | |
| A61B 1/00 | (2006.01) | |
| A61B 1/24 | (2006.01) | |
| A61B 6/14 | (2006.01) | |
| A61C 8/00 | (2006.01) | |
| A61B 90/00 | (2016.01) | |
| A61B 17/00 | (2006.01) | |
| A61B 90/30 | (2016.01) | |

(52) U.S. Cl.
CPC ........... *A61B 6/14* (2013.01); *A61B 34/10* (2016.02); *A61C 1/084* (2013.01); *A61C 1/12* (2013.01); *A61C 3/02* (2013.01); *A61C 8/0089* (2013.01); *A61C 9/0053* (2013.01); *A61B 2017/00946* (2013.01); *A61B 2034/107* (2016.02); *A61B 2034/2055* (2016.02); *A61B 2034/2057* (2016.02); *A61B 2034/2065* (2016.02); *A61B 2034/2072* (2016.02); *A61B 2090/0811* (2016.02); *A61B 2090/309* (2016.02); *A61B 2090/371* (2016.02); *A61B 2090/373* (2016.02); *A61B 2090/3916* (2016.02); *A61B 2090/3937* (2016.02); *A61B 2090/3966* (2016.02); *A61B 2090/3983* (2016.02); *A61B 2090/3987* (2016.02); *A61B 2090/3995* (2016.02)

(58) Field of Classification Search
CPC ....... A61C 9/004; A61C 9/0053; A61B 34/20; A61B 34/10; A61B 6/14; A61B 2034/2005; A61B 90/39
See application file for complete search history.

(56) References Cited

U.S. PATENT DOCUMENTS

| | | | | |
|---|---|---|---|---|
| 5,188,111 | A * | 2/1993 | Yates | A61B 1/0058 128/DIG. 7 |
| 6,332,891 | B1 * | 12/2001 | Himes | A61B 90/36 606/130 |
| 7,643,867 | B2 * | 1/2010 | Solar | A61B 34/20 356/247 |
| 8,320,612 | B2 * | 11/2012 | Knobel | A61C 1/082 348/169 |
| 2002/0077542 | A1 * | 6/2002 | Vilsmeier | A61C 1/084 600/424 |
| 2002/0087179 | A1 * | 7/2002 | Culp | A61B 90/98 606/167 |
| 2006/0240378 | A1 * | 10/2006 | Weinstein | A61B 5/103 433/76 |
| 2009/0068620 | A1 * | 3/2009 | Knobel | A61C 1/082 433/223 |
| 2009/0136902 | A1 * | 5/2009 | Zundorf | A61C 8/0089 433/223 |
| 2010/0035201 | A1 * | 2/2010 | Beck | A61C 1/084 433/76 |
| 2010/0323320 | A1 * | 12/2010 | Takebayashi | A61C 1/084 433/75 |
| 2011/0159455 | A1 * | 6/2011 | Stumpel | A61C 1/084 433/60 |
| 2012/0015329 | A1 * | 1/2012 | Gross | A61C 1/084 433/215 |
| 2012/0040305 | A1 * | 2/2012 | Karazivan | A61B 1/00087 433/29 |
| 2012/0251978 | A1 * | 10/2012 | Katz | A61C 8/0001 433/196 |
| 2012/0266898 | A1 | 10/2012 | Vogele | |
| 2013/0017507 | A1 * | 1/2013 | Moffson | A61C 1/084 433/27 |
| 2013/0209953 | A1 * | 8/2013 | Arlinsky | A61C 1/082 433/27 |
| 2014/0107471 | A1 * | 4/2014 | Haider | A61B 17/1703 600/424 |
| 2014/0147807 | A1 * | 5/2014 | Yau | A61C 1/084 433/173 |
| 2014/0178832 | A1 * | 6/2014 | Choi | A61C 1/084 433/27 |
| 2014/0186794 | A1 * | 7/2014 | Deichmann | A61B 17/176 433/75 |
| 2014/0199650 | A1 * | 7/2014 | Moffson | A61C 1/082 433/27 |
| 2014/0236159 | A1 * | 8/2014 | Haider | A61B 17/1626 606/88 |
| 2014/0272789 | A1 * | 9/2014 | Mozes | A61C 8/0092 433/173 |
| 2014/0377716 | A1 * | 12/2014 | Rauscher | A61B 5/0088 433/29 |
| 2016/0135762 | A1 * | 5/2016 | Mihailescu | A61B 6/027 600/424 |
| 2016/0183776 | A1 * | 6/2016 | Yamanaka | A61C 1/08 433/29 |

FOREIGN PATENT DOCUMENTS

| | | |
|---|---|---|
| EP | 2 236 104 B1 | 10/2010 |
| JP | 2007-203075 A | 8/2007 |
| JP | 2010-104652 A | 5/2010 |
| WO | WO 2006/131373 A2 | 12/2006 |
| WO | WO 2012/068679 A1 | 5/2012 |
| WO | WO 2013/052187 A2 | 4/2013 |
| WO | WO 2013/053398 A1 | 4/2013 |
| WO | WO 2013053398 A1 * | 4/2013 ............. H04N 7/183 |

OTHER PUBLICATIONS

International Preliminary Report on Patentability for Application No. PCT/EP2013/070553, dated Sep. 16, 2015.

* cited by examiner

NAVIGATION SYSTEM AND METHOD FOR DENTAL AND CRANIO-MAXILLOFACIAL SURGERY, POSITIONING TOOL AND METHOD OF POSITIONING A MARKER MEMBER

CROSS REFERENCE TO RELATED APPLICATIONS

This application is a national stage filing under 35 U.S.C. § 371 of International PCT Application No. PCT/EP2013/070553, filed Oct. 2, 2013, the entire contents of which is incorporated herein in its entirety.

FIELD OF THE INVENTION

The invention relates to a navigation system for dental and cranio-maxillofacial surgery comprising a marker member and to a navigation method using this navigation system. Further, the invention relates to a positioning tool for use with the navigation system and to a method of positioning the marker member of the navigation system on a patient's tooth or teeth.

BACKGROUND ART

About 5 million dental implant procedures were carried out in Europe in 2012. Approximately 18% of these procedures were performed with the use of treatment planning software and approximately 4% of these procedures used mechanical drilling templates as tool for guided surgery.

The use of such drilling templates is still limited because the production thereof is complex, time-consuming (about 3 to 10 days) and expensive (about 300 to 700 FUR per template). Moreover, the overall precision with drilling templates is limited to approximately 1 to 2 mm and the ergonomic situation for the surgeon is not satisfactory, due to the problem of a blocked view during surgery.

EP 2 236 104 B1 discloses a method and a device for medical navigation in which the positional relationship of an instrument with respect to a part of a patient's body is ascertained.

The device comprises an image output on which the instrument and the part of the patient's body are displayed in the correct positional relationship, and an image processor which generates a display of the part of the patient's body on the basis of virtual image data captured by means of a medical imaging method and on the basis of actual images captured during navigation. The device further comprises an image display control which displays the virtual image data on the image output primarily and as the basis of the image, wherein the actual images are superimposed on the virtual image data merely as an addition and secondarily.

The actual images are provided by a video image capture unit which is fixedly arranged on the instrument. The positional relationship of the instrument with respect to the part of the patient's body is ascertained by a stationary tracking system having two cameras and two reference assemblies, one assembly being placed on the part of the patient's body and the other assembly being placed on the instrument. In order to detect this positional relationship at any time during surgery, the two reference assemblies always have to be within the field of vision of the tracking system.

However, the use of the tracking system and the two reference assemblies renders the above device complex. Further, the requirement of the two reference assemblies constantly being located within the field of vision of the stationary tracking system imposes limitations on the applicability of the device. Specifically, in dental and cranio-maxillofacial surgery, in particular, in intraoral applications, in which the area to be treated is arranged within the patient's oral cavity, this requirement may be difficult or even impossible to fulfil, at least throughout the entire surgical procedure.

Hence, there remains a need for a navigation system and a navigation method for dental and cranio-maxillofacial surgery which enable precise surgical navigation in a simple and reliable manner.

SUMMARY OF THE INVENTION

One object of the invention is to provide a navigation system and a navigation method for dental and cranio-maxillofacial surgery which allow for precise surgical navigation in a simple and reliable manner. Further, the invention aims to provide a positioning tool for use with this navigation system which enables accurate positioning of a marker member on a patient's tooth or teeth and a positioning method using this positioning tool.

The invention provides a navigation system for dental and cranio-maxillofacial surgery comprising a surgical handpiece or instrument, and imaging unit which is movably attached to the surgical handpiece or instrument, and a marker member which is attachable to a cranial bone, facial bone, a tooth or teeth of a patient.

The marker member comprises a plurality of marker elements, such as reference lines and/or reference points, which are detectable by the imaging unit.

The plurality of marker elements may be separate elements or elements which are at least partly connected or joined to each other. The marker elements may be provided to the marker member so as to be separate from each other. The marker elements may be provided to the marker member so that at least some or all of the marker elements are at least partly connected or joined to each other, e.g., so as to form a continuous pattern, such as an optical pattern.

The imaging unit is movably attached, mounted or installed to the surgical handpiece or instrument, so as to be movable relative to the surgical handpiece or instrument. The imaging unit can thus be moved independently from the surgical handpiece.

The imaging unit may be movably attached to the surgical handpiece or instrument so as to be continuously, e.g., steplessly, movable relative to the handpiece or instrument. The imaging unit may be movably attached to the surgical handpiece or instrument so as to be movable relative to the handpiece or instrument in discrete steps or stages.

The marker member is attachable, mountable, fixable, installable or securable to a component of the patient's cranium, skull or teeth, such as a cranial bone, a facial bone, a tooth or a plurality of teeth. The marker member is thus configured so that it can be attached, mounted, fixed, installed or secured to a cranial bone, a facial bone, a tooth or teeth of the patient. Before the start of a surgical procedure, the marker member is attached to the cranial bone, the facial bone, the tooth or the teeth of the patient in the area in which surgery is to be performed.

The imaging unit is configured to obtain or provide imaging data, i.e., imaging data of the area in which surgery is performed, in particular, to obtain or provide imaging data of the area of surgery in real time. In this way, imaging data of the area of surgery can be provided in real time, thus assisting the surgeon during the surgical procedure in a precise manner.

The imaging unit is configured to detect the plurality of marker elements of the marker member. During surgery, the marker elements are detected by the imaging unit. Since the imaging unit is attached to the surgical handpiece or instrument and the marker member comprising the marker elements is attached to the cranial bone, facial bone, tooth or teeth in the area in which surgery is performed, detection of the marker elements by the imaging unit allows for the position of the handpiece or instrument relative to the area of surgery to be accurately determined.

In particular, since the imaging unit is movably attached to the surgical headpiece or instrument, the imaging unit can be moved relative to the handpiece or instrument, so that a substantially permanent contact, e.g., visual contact, between the imaging unit and the marker elements can be ensured at any time during surgery. In this way, it can be assured that the marker elements of the marker member are substantially constantly detected by the imaging unit throughout a surgical procedure.

If it is determined that the plurality of marker elements are not detected by the imaging unit, the imaging unit can be moved relative to the surgical handpiece or instrument to a position in which the imaging unit detects the plurality of marker elements.

Therefore, the navigation system of the invention enables precise navigation during dental and cranio-maxillofacial surgery in a simple and reliable manner.

Further, the movable attachment of the imaging unit to the surgical handpiece or instrument considerably improves ergonomics for the surgeon. In particular, since the imaging unit is movable relative to and independently from the handpiece or instrument, the handpiece or instrument can be freely operated by the surgeon without the risk of losing contact between the imaging unit and the marker elements.

Due to the achievement of precise navigation during surgery and the improved ergonomics for the surgeon, clinical safety and clinical outcome are significantly enhanced. Since there is no need for the production of mechanical drilling guides, the costs for the surgical procedure can be significantly reduced.

The navigation system can be used particularly advantageously in intraoral applications, such as tooth removal or replacement, dental implants etc. In such applications, the area of surgery is arranged within the patient's oral cavity. Further, at least for a substantial time during surgery, also a portion of the surgical handpiece or instrument is disposed in this cavity. The relative position of the handpiece or instrument and the area of surgery is thus difficult to monitor from outside the cavity, e.g., by using conventional tracking systems. This problem is overcome by using the movably attached imaging unit and the marker member of the inventive navigation system.

Moreover, due to the limited space available to the surgeon in intraoral applications, the improved ergonomics achieved by the navigation system of the invention are particularly beneficial.

The imaging unit may be configured to more relative to the surgical handpiece or instrument so as to substantially constantly or permanently maintain contact, e.g., visual contact, with the plurality of marker elements, in particular, in use of the navigation system.

The navigation system may comprise a sensor and/or detector for sensing or detecting whether the marker elements are detected by the imaging unit.

The navigation system may comprise an actuator or drive element for moving the imaging unit relative to the surgical handpiece or instrument.

The actuator or drive element may be configured to move the imaging unit relative to the surgical handpiece or instrument to a position in which the imaging unit detects the plurality of marker elements, e.g., if it is determined, for example, sensed or detected by the sensor and/or detector, that the plurality of marker elements are not detected by the imaging unit.

The navigation system may comprise a single imaging unit or a plurality of imaging units, such as two, three, four or more imaging units. The imaging units may be arranged in different positions on the surgical handpiece or instrument, e.g., along the length and/or around the circumference of the surgical handpiece or instrument.

The imaging unit may comprise one or more camera units, e.g., one or more stereoscopic camera units, and/or one or more 3D scanners, such as laser scanners, or the like. The imaging unit may be capable of imaging, i.e., obtaining or providing imaging data, in the visible and/or infrared light spectrum. The imaging unit may be configured to obtain or provide three-dimensional imaging data of the area of surgery.

The 3D scanner may be a 3D surface scanner. The 3D surface scanner may be configured to optically scan the surface of the area in which surgery is performed, e.g., the surface of a cranial bone, a facial bone, a tooth or teeth of the patient. In this way, the position of the patient can be monitored in a particularly precise and reliable manner.

The imaging unit may be removably attached to the surgical handpiece or instrument. In this case, the imaging unit can be removed or detached from the surgical handpiece or instrument. By using such a modular configuration of the imaging unit and the surgical handpiece or instrument, the imaging unit can be attached to and used in combination with different surgical handpieces or instruments. Thus, a single imaging unit can be used for a variety of different surgical procedures, thereby further reducing the costs of surgery.

The navigation system may further comprise a light source, such as an LED, a laser pointer or the like, which may be arranged on the imaging unit, e.g., for illuminating the marker elements of the marker member. In this way, the detection process of the marker elements by the imaging unit can be further improved.

The imaging unit may be lockable or arrestable relative to the surgical handpiece in a plurality of different positions relative to the surgical handpiece. For example, the imaging unit may be lockable in a plurality of different longitudinal and/or lateral and/or angular positions relative to the surgical handpiece. The navigation system may comprise a locking or arrestingelement for locking or arresting the imaging unit in the plurality of positions relative to the surgical handpiece.

The imaging unit may be lockable or arrestable in a plurality of discrete or continuous positions relative to the surgical handpiece. In particular, the imaging unit may be movably attached to the surgical handpiece so as to be continuously, e.g., steplessly, movable relative to the handpiece and lockable in every achievable position relative to the handpiece.

By locking or arresting the imaging unit in a position relative to the surgical handpiece, i.e., locking or arresting the imaging unit so that it is immobilised relative to the handpiece, the imaging unit can be stably and robustly kept in a well-defined position relative to the handpiece.

Such an arrangement allows for a particularly precise measurement or detection of the position of the surgical handpiece relative to the marker elements of the marker member.

The imaging unit may be configured to move relative to the surgical handpiece only if it is determined that the plurality of marker elements are net detected by the imaging unit. In this case, the imaging unit may be configured to move relative to the surgical handpiece to a position in which the imaging unit detects the plurality of marker elements and to be locked or arrested in this position.

The navigation system may further comprise a sensor and/or detector unit for sensing or detecting the position of the imaging unit relative to the surgical handpiece. In this way, the position of the surgical handpiece relative to the marker elements of the marker member can be determined in a particularly precise and reliable manner. The sensor and/or detector unit may be any type of sensor and/or detector capable of position detection, such as a piezoelectric sensor or detector.

The sensor and/or detector unit may be configured to detect the position of the imaging unit relative to the surgical handpiece in a discrete manner, i.e., for a plurality of discrete different positions, or in a continuous manner, i.e., for a plurality of continuous different positions. The sensor and/or detector unit may be configured to detect a longitudinal and/or lateral and/or angular position of the imaging unit relative to the surgical handpiece.

The imaging unit may be slidably, pivotably and/or rotatably attached to the surgical handpiece, so as to be slidable, pivotable and/or rotatable, respectively, relative to the surgical handpiece.

The imaging unit may be slidable, pivotable and/or rotatable relative to the surgical handpiece in one or more linear and/or angular directions. The imaging unit may be slidable along a length of the surgical handpiece and/or along a direction perpendicular to the length, i.e., the longitudinal axis, of the handpiece and/or rotatable around the longitudinal axis of the handpiece and/or around an axis which is perpendicular to the longitudinal axis of the handpiece.

The imaging unit may be slidable along the entire length of the surgical handpiece or along a portion of the length of the surgical handpiece. The imaging unit may be rotatable relative to the surgical handpiece over an angular range of more than 45°, preferably more than 90°, more preferably more than 180°, even more preferably more than 270° and yet even more preferably 360°.

Rotatably attaching the imaging unit to the surgical handpiece provides a simple arrangement which allows for a wide imaging area to be covered by the imaging unit, thereby ensuring in a simple manner that the marker elements of the marker member are detected by the imaging unit substantially at any time during surgery.

Further, by rotatably attaching the imaging unit to the surgical handpiece so as to be rotatable relative to the handpiece around an axis perpendicular to the longitudinal axis of the handpiece, permanent detection of the marker elements can be ensured, while any interference of the movement of the imaging unit with the operation of the surgical handpiece by the surgeon is particularly reliably prevented.

The imaging unit may comprise one or more display members, such as miniature displays. The one or more display members may be configured for displaying data, such as imaging data and/or treatment planning data. The one or more display members may be arranged on a rear side of the imaging unit, opposite to a front side of the imaging unit which is configured to face the marker member in use of the navigation system.

The marker member or a body thereof may be at least partly made of a rigid, stiff, inflexible and/or hard material. The marker member or a body thereof may be at least partly made of a flexible, resilient, deformable, e.g., permanently deformable, soft and/or elastic material. The marker member or a body thereof may be made of plastic, metal, ceramic or the like.

The marker member may comprise an attachment element enabling attachment to a cranial bone, a facial bone, a tooth or teeth of a patient, such as a screw element, a clamp element, an adhesive element or the like.

The marker member may comprise a radiopaque material, i.e., a material which does not transmit X-ray radiation therethrough. The marker member may comprise one or more radiopaque elements, such as radiopaque beads, radiopaque wires, radiopaque plates or the like. The radiopaque material may be lead, titanium, tungsten etc. or a combination thereof.

The radiopaque material may be disposed within the body of the marker member and/or on a surface of the marker member. One or more of the plurality of marker elements may be made from a radiopaque material.

The radiopaque material is visible by X-ray imaging techniques, such as computer tomography (CT), e.g., cone beam CT. Hence, the marker member comprising the radiopaque material can be used as a reference for X-ray imaging, in particular, X-ray imaging prior to a surgical procedure.

The marker member may be attached to a cranial bone, a facial bone, a tooth or teeth of the patient prior to X-ray imaging. Subsequently, X-ray imaging, such as CT, e.g., cone beam CT, may be performed for obtaining X-ray imagining data using the radiopaque material of the marker member as a reference. The marker member may be maintained in its position in the subsequent surgical procedure, wherein the marker elements thereof serve as a reference for the imaging unit.

In this case, the marker member serves as a reference for imaging both before and during surgery, thus allowing for a particularly simple configuration of the navigation system.

Further, providing the marker member with a radiopaque material allows for diagnostics using X-ray imaging, such as cone beam CT, treatment planning and guided surgery to be performed in one visit of the patient in a particularly simple manner, thereby also further reducing the duration and the costs of the treatment.

Moreover, using the marker member as a reference for X-ray imaging prior to surgery and for imaging with the imaging unit during surgery allows for the X-ray imaging data and the imaging data obtained by the imaging unit to be combined, e.g., superposed or overlaid, in a particularly simple and reliable manner, enabling the generation of precise and reliable three-dimensional image data of the area in which surgery is performed.

The marker elements may be provided to the marker member, in particular, on a surface of the marker member, by printing, embossing, etching, engraving or the like. The marker elements may be integrally formed with the body of the marker member. The marker elements may be separate elements which are attached, fixed, secured or mounted to the body of the marker member. For example, the marker elements may be at least partially embedded in the body of the marker member.

The plurality of marker elements may be arranged in a two dimensional pattern or array, e.g., a two-dimensional optical pattern or array. The term "two-dimensional" defines that the marker elements are arranged in a common plane. Such an arrangement of the marker elements allows for a particularly simple configuration of the marker member. Any change in the position of the surgical handpiece relative to the marker member can be sensed by detecting a corresponding distortion of the two-dimensional pattern or array of the marker elements detected by the imaging unit. Hence, the relative position of the surgical handpiece and the marker member can be determined in a particularly simple, reliable and precise manner.

The navigation system may further comprise a processing unit, such as a CPU or the like, for processing imaging data of the imaging unit, i.e., imaging data obtained by the imaging unit. The processing unit may be configured to process imaging data of the imaging unit. The processing unit may be configured to relate the imaging data of the imaging unit to other patient data, such as imaging data, obtained prior to or during the surgical procedure, e.g., using the marker member as a reference.

The processing unit may be configured to combine, e.g., superpose or overlay, the imaging data of the imaging unit with other data, in particular, other imaging data, e.g., other imaging data obtained before and/or during the surgical procedure. In particular, the processing unit may be configured to combine, e.g., superpose or overlay, the imaging data of the imaging unit with X-ray imaging data obtained prior to surgery, e.g., using the marker member comprising the radiopaque material as a reference for both the X-ray imaging and the imaging by means of the imaging unit.

By combining, e.g., superposing or overlaying, the X-ray imaging data and the imaging data of the imaging unit, a precise three-dimensional image of the area in which surgery is performed can be obtained in real time, providing particularly precise and reliable guidance to the surgeon during a surgical procedure.

The processing unit may be configured to combine, e.g., superpose or overlay, the imaging data of the imaging unit with treatment planning data, e.g., treatment planning data provided or obtained by surgery planning software.

The processing unit may be configured to combine, e.g., superpose or overlay, the imaging data of the imaging unit with other imaging data, such as the other imaging data detailed above, and with treatment planning data.

Combining, e.g., superposing or overlaying, the imaging data of the imaging unit with the treatment planning data enables the surgeon to reliably navigate the surgical handpiece, e.g., the tip of a surgical drill, along the treatment planning in terms of position and angulation of the handpiece, for example, using a target system.

The imaging unit may comprise one or more display members, e.g., miniature displays, provided on the imaging unit for displaying the treatment planning, e.g., the target system. In particular, the one or more display members may be arranged on a rear side of the imaging unit, opposite to a front side of the imaging unit which is configured to face the marker member in use of the navigation system. In this way, it can be ensured in an efficient and reliable manner that the treatment planning is in the direct view of the surgeon during surgery.

The target system may be configured to indicate the planned position and/or the planned angle of the surgical handpiece, e.g., in relation to a previous treatment planning. For example, the planned position of the surgical handpiece may be the planned entry position of a drill tip or the like.

The target system may be configured to indicate the planned position of the handpiece, for example, by using one or more reticles or hairline crosses, e.g., a double reticle or hairline cross. The target system may be configured to indicate the planned angle of the handpiece, for example, by using a plurality of rings, e.g., two rings.

The surgical handpiece, e.g., a tip portion thereof, such as a drill tip, a drill head or the like, may be used for registering the relative position of the handpiece and the marker member, in particular, when a marker member without radiopaque material is used or when the marker member had not been attached to the area of surgery prior to the X-ray imaging. In this case, precise and reliable navigation is enabled in a particularly simple manner.

The navigation system may further comprise a display unit for displaying imaging data of the imaging unit. The display unit may be configured to display imaging data of the imaging unit. The display unit may comprise any type of display, such as an LCD display, an LED display or the like.

The display unit may be configured to display combined imaging data generated by combining the imaging data of the imaging unit with other data, e.g., with other imaging data, such as imaging data obtained by X-ray imaging, e.g., prior to surgery, and/or with treatment planning data.

Thus, the area of surgery can be displayed on the display unit three-dimensionally and in real time, providing particularly reliable and precise guidance to the surgeon during the surgical procedure.

The display unit may be arranged, for example, next to, e.g., beside or above, the patient's head during surgery, allowing the surgeon to monitor the imaging data on the display unit, while substantially simultaneously observing the area of surgery.

The display unit may be configured to combine, e.g., superpose or overlay, the imaging data of the imaging unit with other data, in particular, other imaging data, e.g., other imaging data obtained before and/or during the surgical procedure. In particular, the display unit may be configured to combine, e.g., superpose or overlay, the imaging data of the imaging unit with X-ray imaging data obtained prior to surgery, e.g., using the marker member comprising the radiopaque material as a reference for both the X-ray imaging and the imaging by means of the imaging unit.

As has been detailed above, by combining, e.g., superposing or overlaying, the X-ray imaging data and the imaging data of the imaging unit, a precise three-dimensional image of the area in which surgery is performed can be obtained in real time, providing particularly precise and reliable guidance to the surgeon during a surgical procedure.

The display unit may be configured to combine, e.g., superpose or overlay, the imaging data of the imaging unit with treatment planning data, e.g., treatment planning data provided or obtained by surgery planning software.

The display unit may be configured to combine, e.g., superpose or overlay, the imaging data of the imaging unit with other imaging data, such as the other imaging data detailed above, and with treatment planning data.

Combining, e.g., superposing or overlaying, the imaging data of the imaging unit with the treatment planning data enables the surgeon, to reliably navigate the surgical handpiece, e.g., the tip of a surgical drill, along the treatment planning in terms of position and angulation of the handpiece, for example, using a target system such as that described above.

The display unit may be configured to display the treatment planning, e.g., the target system. The target system displayed on the display unit may be a target system as detailed above.

The surgical handpiece may be a dental instrument. The surgical handpiece may be a drill, such as a dental drill. In particular, since the imaging unit is movably attached to the surgical handpiece, the navigation system can be used particularly advantageously for intraoral applications, such as tooth removal or replacement, dental implants etc., using dental instruments, such as dental drills.

The invention provides a positioning tool or element for positioning a marker member on a patient's cranial bone, facial bone, e.g., jaw bone, tooth or teeth comprising a die or tray element, such as an impression tray or a partial impression tray, and a marker member, wherein the marker member comprises a plurality of marker elements and a deformable material, the deformable material is releasably received in the die element, and the plurality of marker elements are arranged on a surface of the deformable material which faces the die element. The marker member may further comprise a radiopaque material, e.g., in the form of one or more radiopaque elements, such as radiopaque beads, radiopaque wires or the like.

The invention provides a positioning tool or element for use with the navigation system of the invention. The positioning tool is configured for positioning the marker member of the navigation system on a patient's cranial bone, facial bone, e.g., jaw bone, tooth or teeth. The positioning tool comprises a die or tray element, such as an impression tray or a partial impression tray, and the marker member. The marker member comprises a deformable, e.g., permanently deformable, material. The deformable material may form a body of the marker member. The deformable material is releasably received in the die element. The plurality of marker elements are arranged on a surface of the deformable material which faces the die element.

The positioning tool or element may be configured for attaching the marker member to the patient's cranial bone, facial bone, e.g., jaw bone, tooth or teeth. The die or tray element is configured for placement over at least part of the patient's cranial bone, facial bone, e.g., jaw bone, tooth or teeth. In particular, the die or tray element is sized and shaped so that it fits over at least part of the patient's cranial bone, facial bone, e.g., jaw bone, tooth or teeth. The die or tray element is configured for receiving the deformable material.

The deformable material is releasably received in the die element, i.e., received in the die element so that it can be released, e.g., removed or separated, therefrom, e.g., by removing the die element from the at least part of the patient's cranial bone, facial bone, e.g., jaw bone, tooth or teeth.

The deformable material is conformable to the patient's cranial bone, facial bone, e.g., jaw bone, tooth or teeth, i.e., configured so that it can conform to the patient's cranial bone, facial bone, e.g., jaw bone, tooth or teeth when placing the die element over at least part of the patient's cranial bone, facial bone, e.g., jaw bone, tooth or teeth. The deformable material may be permanently deformable.

The deformable material may be at least partly adhesive so as to adhere to the at least part of the patient's cranial bone, facial bone, e.g., jaw bone, tooth or teeth. The deformable material may be configured to adhere to the at least part of the patient's cranial bone, facial bone, e.g., jaw bone, tooth or teeth at least by a form fit or positive fit between the deformable material and the at least part of the cranial bone, facial bone, e.g., jaw bone, tooth or teeth.

The deformable material may be configured to harden or cure, e.g., by exposure to air, such as ambient air, and/or by exposure to ultraviolet (UV) light or the like. The deformable material may be a resin, such as a plastic resin, e.g., a curable resin. The deformable material may be an impression paste, e.g., a hardenable or curable impression paste.

The marker elements may be at least partially embedded in the deformable material. The marker elements may be printed, embossed or otherwise formed on a surface of the deformable material which faces the die element. The surface of the deformable material which faces the die element may be in contact with the die element.

By using the positioning tool of the invention, the marker member can be positioned on a patient's cranial bone, facial bone, e.g., jaw bone, tooth or teeth and attached thereto in a particularly simple and reliable manner. In particular, the marker member is fixedly held in its position on the patient's cranial bone, facial bone, e.g., jaw bone, tooth or teeth by the deformable material, so that no clamping, screwing etc. of the marker member is necessary. Therefore, any damage to the patient's cranial bone, facial bone, e.g., jaw bone, tooth or teeth due to the attachment of the marker member is reliably prevented.

The invention further provides a set of positioning tools comprising four positioning tools, wherein the die or tray elements, such as impression trays or partial impression trays, of the four positioning tools have different shapes and/or sizes from each other. For example, each die or tray element of the four positioning tools may be configured for placement over a different quadrant of the human or animal jaw, e.g., over the teeth of a different quadrant of the human or animal jaw. In particular, the set of positioning tools may comprise four positioning tools, wherein the die or tray elements are different partial impression trays for different quadrants of the human or animal jaw.

By using such a set of positioning tools, the appropriate positioning tool corresponding to the location or area in which the surgery is to be performed, such as the upper or lower jaw, a particular jaw quadrant etc., can be selected, thus allowing for a particularly precise positioning of the marker member.

The navigation system of the invention may further comprise the positioning tool or the set of positioning tools of the invention.

The invention further provides a method of positioning a marker member on a patient's cranial bone, facial bone, e.g., jaw bone, tooth or teeth using the positioning tool of the invention. The method comprises the steps of placing the die or tray element with the deformable material received therein over at least part of the patient's cranial bone, facial bone, e.g., jaw bone, tooth or teeth so as to attach the deformable material to at least part of the patient's cranial bone, facial bone, e.g., jaw bone, tooth or teeth, and removing the die or tray element from the at least part of the patient's cranial bone, facial bone, e.g., jaw bone, tooth or teeth so as to release the deformable material from the die or tray element.

The method of positioning the marker member of the invention provides the advantageous effects already described in detail above for the positioning tool of the invention. In particular, the method enables a reliable and precise positioning of the marker member, avoiding any damage to the patient's cranial bone, facial bone, e.g., jaw bone, tooth or teeth due to the attachment of the marker member.

The method of positioning the marker member of the invention is a method of using the positioning tool of the invention. Hence, the further features disclosed in connection with the above description of the positioning tool of the invention may also be applied to the positioning method of the invention.

The invention further provides a navigation method for dental and cranio-maxillofacial surgery using the navigation system of the invention. The navigation method comprises the steps of imaging at least part of the area in which surgery is performed by means of the imaging unit, determining whether the plurality of marker elements are detected by the imaging unit, and, if it is determined that the plurality of marker elements are not detected by the imaging unit, moving the imaging unit relative to the surgical handpiece or instrument to a position in which the imaging unit detects the plurality of marker elements.

The navigation method of the invention provides the advantageous effects already described in detail above for the navigation system of the invention. In particular, the navigation method enables precise surgical navigation during dental and cranio-maxillofacial surgery in a simple and reliable manner. The method allows for the relative position between the surgical handpiece or instrument and the marker member to be precisely determined in a simple and reliable way.

The navigation method may further comprise the step of locking or arresting the imaging unit in one or more positions relative to the surgical handpiece.

The navigation method may further comprise the step of detecting or sensing the position of the imaging unit relative to the surgical handpiece.

The navigation method may comprise the step of sliding, pivoting or rotating the imaging unit relative to the surgical handpiece, e.g., to a position in which the imaging unit detects the plurality of marker elements.

The navigation method may further comprise the step of processing imaging data of the imaging unit. The navigation method may comprise the step of combining, e.g., superposing or overlaying, the imaging data of the imaging unit with other data, e.g., with other imaging data, such as X-ray imaging data, e.g., cone beam CT data, obtained prior to surgery, and/or with treatment planning data.

The navigation method may further comprise the step of displaying imaging data of the imaging unit, e.g., a combination of imaging data of the imaging unit with X-ray imaging data obtained prior to surgery and/or with treatment planning data, for example, on a display unit.

The navigation method may further comprise the step of attaching, securing, fixing, mounting or installing the marker member to a cranial bone, a facial bone, a tooth or teeth of a patient, e.g., prior to surgery or prior to X-ray imaging performed before surgery.

The navigation system may further comprise a step of positioning the marker member on a patient's cranial bone, facial bone, e.g., jaw bone, tooth or teeth using the positioning tool of the invention. In particular, the navigation method may comprise the steps of placing the die element with the deformable material received therein over at least part of the patient's cranial bone, facial bone, e.g., jaw bone, tooth or teeth so as to attach the deformable material to at least part of the patient's cranial bone, facial bone, e.g., jaw bone, tooth or teeth, and removing the die element from the at least part of the patient's cranial bone, facial bone, e.g., jaw bone, tooth or teeth so as to release the deformable material from the die element.

The navigation method may further comprise the step of registering the position of the surgical handpiece by touching the marker member with the surgical handpiece, e.g., with a tip portion thereof.

The navigation method of the invention is a method of using the navigation system of the invention. Therefore, the further features disclosed in connection with the above description of the navigation system of the invention may also be applied to the navigation method of the invention.

BRIEF DESCRIPTION OF DRAWINGS

Hereinafter, non-limiting examples of the invention are explained, with reference to the drawings, in which.

DETAILED DESCRIPTION OF CURRENTLY PREFERRED EMBODIMENTS

Figure 1:
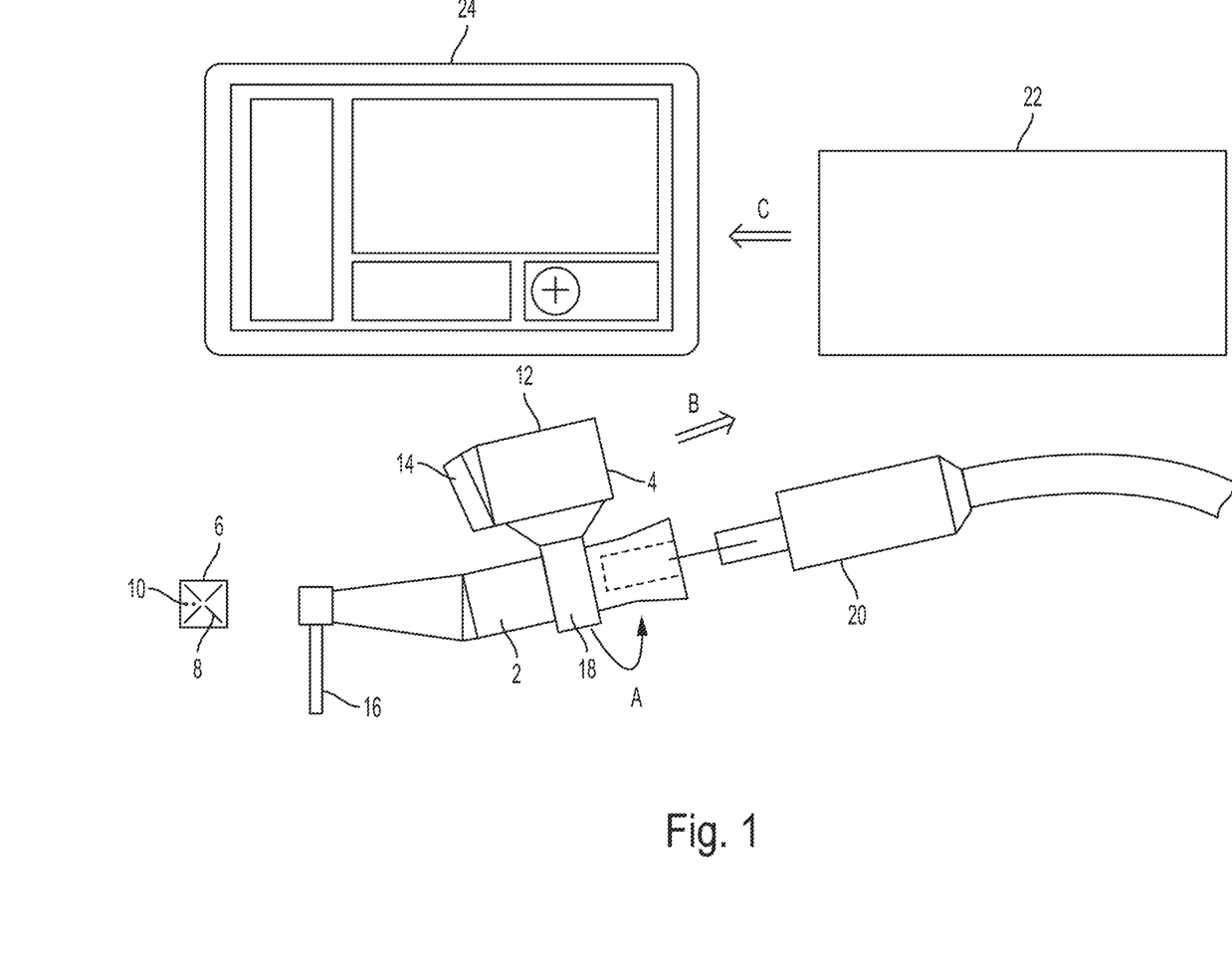
FIG. 1 shows a schematic side view of a navigation system according to an embodiment of the present invention.

FIG. 1 shows a schematic side view of a navigation system for dental and cranio-maxillofacial surgery according to a currently preferred embodiment of the present invention.

The navigation system comprises a surgical handpiece, namely a dental drill 2, an imaging unit 4 which is movably attached to the drill 2 and a marker member 6 which is attachable to a cranial bone, a facial bone, a tooth or teeth of a patient. The marker member 6 comprises a plurality of marker elements, namely reference lines 8 and reference points 10, which are detectable by the imaging unit 4.

The reference lines 8 and the reference points 10 are printed onto a surface of a body of the marker member 6 and arranged in a two-dimensional optical pattern. The body of the marker member 6 is made of a rigid material, such as hard plastic, metal, ceramic or the like. The marker member 6 further comprises an attachment element (not shown), such as a screw element, a clamp element, an adhesive element or the like, for attaching the marker member 6 to a cranial bone, a facial bone, a tooth or teeth of the patient.

Further, the marker member 6 comprises a radiopaque material in the form of a plurality of radiopaque beads (not shown) made from titanium or tungsten which are disposed within the body of the marker member 6.

The imaging unit 4 comprises a camera unit 12 capable of imaging in the visible light spectrum and an optical 3D surface scanner 14 for optically scanning the surface of the patient's teeth or bone structure. The imaging unit 4 is configured to detect the marker elements 8, 10 of the marker member 6.

The imaging unit 4 comprises an electronic device (not shown), such as a chipset, for pre-processing data, such as imaging data, provided by the camera unit 12. In particular, the data may be pre-processed by performing a data reduction, e.g., using a region of interest.

The imaging unit 4 is rotatably attached to the drill 2 through an attachment member 18, so as to be rotatable relative to the drill 2 around a longitudinal axis of the drill 2, as is indicated by arrow A in FIG. 1. The imaging unit 4 is continuously rotatable relative to the drill 2 over an angular range of 360° and lockable relative to the drill 2 in any angular position.

The imaging unit 4 may be arranged so as to be rotatable relative to the drill 2 around one or more axes perpendicular to the longitudinal axis of the drill 2 or rotatable both around the longitudinal axis and one or more axes perpendicular to the longitudinal axis.

The attachment member 18 comprises a sensor unit (not shown), such as a piezoelectric sensor, for detecting the angular position of the imaging unit 4 relative to the drill 2 and a drive element (not shown), such as an electric motor, for rotating the imaging unit 4 relative to the drill 2 around the longitudinal axis of the drill 2.

The drill 2 comprises a drill head or drill tip 16. The drill 2 is connectable to a surgical micro-motor 20 for supplying power to the drill 2, driving the drill tip 16 so as to rotate.

The navigation system according to the embodiment shown in FIG. 1 further comprises a processing unit 22 and a display unit 24. The imaging unit 4 is configured to transmit, by wired or wireless transmission, imaging data of the area of surgery, including the marker elements 8, 10 of the marker member 6, to the processing unit 22, as is indicated by arrow B in FIG. 1.

The processing unit 22 is configured to further process the pre-processed imaging data transmitted thereto by the imaging unit 4. In particular, the processing unit 22 is configured to perform a 6D-processing of the imaging data.

Further, the processing unit 22 is configured to wirelessly transmit the processed imaging data in real time to the display unit 24, as is indicated by arrow C in FIG. 1.

The display unit 24 is configured to combine this processed imaging data of the processing unit 22 with imaging data obtained in X-ray imaging, such as cone beam CT, performed prior to surgery, and with treatment planning data provided by surgery planning software. In particular, the display unit 24 is configured to combine the processed imaging data of the processing unit 22 and the imaging data of the X-ray imaging using the marker member 6 as a reference for both the imaging data obtained by the imaging unit and the X-ray imaging data, thereby generating three-dimensional imaging data of the area of surgery in real time.

Further, the display unit 24 is configured to display the combined imaging data three-dimensionally and in real time. The display unit 24 displays a target system, such as the target system detailed above, based on the treatment planning data, enabling the surgeon to reliably navigate the drill 2, e.g., the tip 16 thereof, along the treatment planning in terms of position and angulation.

In the following, an example of the operation of the navigation system shown in FIG. 1, exemplifying an embodiment of the navigation method of the invention, will be described with reference to FIG. 2.

Figure 2:
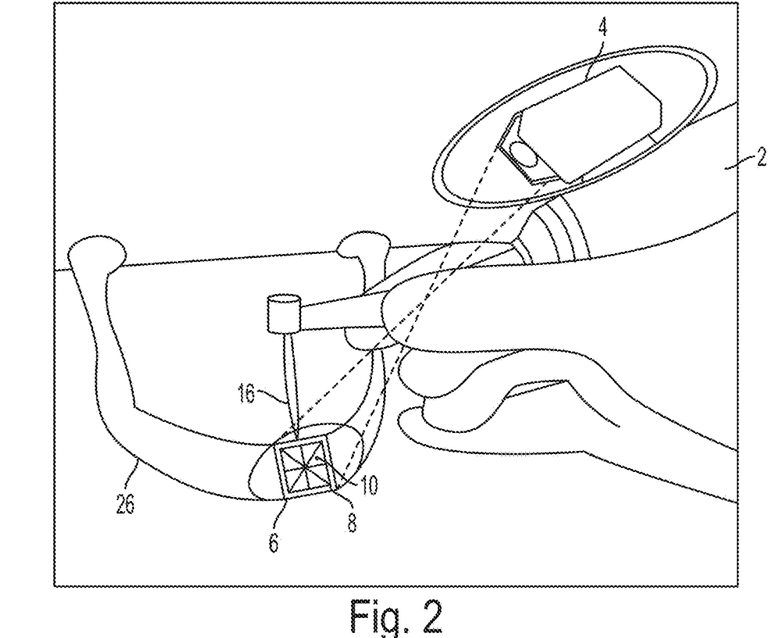
FIG. 2 shows a perspective view of the navigation system shown in FIG. 1.

First, as is shown in FIG. 2, the marker member 6 is attached to the jaw bone 26 of the patient in the area in which surgery is to be performed, by using the attachment element thereof. Subsequently, the patient is subjected to X-ray imaging, such as cone beam CT, thereby obtaining X-ray imaging data of the area of surgery, using the radiopaque material of the marker member 6 as a reference. The X-ray imaging data obtained in this way is stored in a memory (not shown) of the display unit 24.

When starting the surgical procedure, the imaging unit 4 is rotated relative to the drill 2 so as to detect the marker elements 8, 10 of the marker member 6 attached to the jaw bone 26, as is indicated by dashed lines in FIG. 2. The imaging unit 4 images at least part of the area in which surgery is performed and transmits the obtained imaging data to the processing unit 22 in real time.

The processing unit 22 is configured to determine whether the plurality of marker elements 8, 10 are detected by the imaging unit 4. If it is determined by the processing unit 22 that the marker elements 8, 10 are not detected by the imaging unit 4, the imaging unit 4 is rotated relative to the drill 2 around the longitudinal axis thereof by the drive element of the attachment member 18 to a position in which the imaging unit 4 detects the marker elements 8, 10. The imaging unit 4 is locked in this position relative to the drill 2 by the attachment member 18.

In this way, it is ensured that the marker elements 8, 10 are detected by the imaging unit 4 substantially throughout the surgical procedure, so that the relative position between the drill 2 and the marker elements 8, 10 of the marker member 6, and thus the area of surgery, can be reliably determined at any time during the surgical procedure.

The imaging data transmitted by the imaging unit 4 to the processing unit 22 in real time is further processed and wirelessly transmitted to the display unit 24 by the processing unit 22. In the display unit 24, the processed imaging data is combined, i.e., superposed or overlaid, with the treatment planning data and with the X-ray imaging data stored in the memory of the display unit 24, using the radiopaque material and the marker elements 8, 10 of the marker member 6 as a reference, thereby generating real time three-dimensional imaging data of the area in which surgery is performed.

The three-dimensional real time imaging data thus generated and the target system based on the treatment planning data are displayed to the surgeon by the display unit 24. In particular, the display unit 24 may be arranged next to, e.g., beside or above, the patient's head during surgery, allowing the surgeon to substantially simultaneously observe the area of surgery and follow the real time three dimensional imaging data and the target system displayed on the display unit 24. Alternatively or additionally, the target system may be displayed on one or more display members (not shown), e.g., miniature displays, provided on the imaging unit 4. In particular, the one or more display members may be arranged on a rear side of the imaging unit 4, opposite to a front side of the imaging unit 4 where the optical 3D surface scanner 14 is provided.

In this way, the surgeon is precisely and reliably guided by the navigation system during the surgical procedure.

Figure 3:
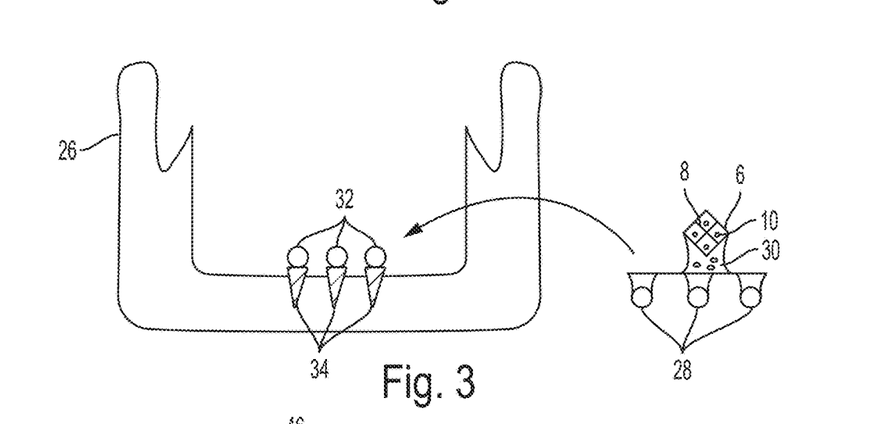
FIG. 3 shows a schematic cross-sectional view of a marker member according to an embodiment of the present invention in a partly detached state from a patient's jaw.

FIG. 3 shows a schematic cross-sectional view of the patient's jaw bone 26, illustrating an attachment element of the marker member 6 and a method of attaching the marker member 6 to the jam bone 26.

The marker member 6 comprises a plurality of recesses or sockets 28, namely three sockets 28 in the embodiment shown in FIG. 3, which are attached to a bottom portion of the body of the marker member 6 through a connection element 30. The sockets 28 are configured for receiving heads 32 of screws 34. The sockets 28 and the screws 34 together form the attachment element of the marker member 6.

The screws 34 are screwed into the jaw bone 26 of the patient, as is schematically shown an FIG. 3. Subsequently, the marker member 6 is placed on top of the screws 34, so that the screw heads 32 are received within the sockets 28, thereby fixedly attaching the marker member 6 to the screws 34 and thus also the jaw bone 26.

In this way, the marker member 6 can be securely and reliably attached directly to the jaw bone 26. Hence, the marker member 6 of the embodiment shown in FIG. 3 can be used particularly advantageously for edentulous or toothless patients.

Figure 4:
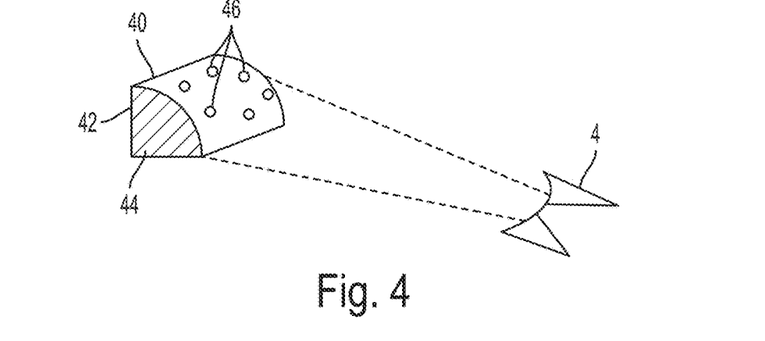
FIG. 4 shows a schematic perspective view of a positioning tool of an embodiment of the present invention.

FIG. 4 shows a schematic perspective view of a positioning tool 40 according to an embodiment of the present invention.

The positioning tool 40 comprises a die element 42, such as an impression tray or a partial impression tray, and a marker member. The marker member comprises a deformable material 44 as a body thereof, as is indicated by the hatching in FIG. 4, and a plurality of marker elements 46. The deformable material 44 is releasably received in the die element 42. The plurality of marker elements 46 are arranged on a surface of the deformable material 44 which faces the die element 42, i.e., an inner surface of the die element 42.

The deformable material 44 is a hardenable or curable paste, such as an impression paste. The deformable material 44 is deformable so as to conform, for example, to the teeth of the patient. The marker elements 46 are made of metal, ceramic, plastic or the like and have a color which is different from that of the deformable material 44.

The marker elements 46 are partially embedded in the deformable material 44 so as to be visible on the surface thereof, thus forming an optically visible pattern which is detectable by the imaging unit 4, in particular, the camera unit 12. The deformable material 44 and the marker elements in combination form the marker member according to the embodiment of the present invention shown in FIG. 4.

In the following, an example of the operation of the positioning tool 40 shown in FIG. 4, exemplifying an embodiment of the method of the invention of positioning the marker member on a patient's cranial bone, facial bone, tooth or teeth, will be explained.

The die element 42 with the deformable material 44 releasably received therein is placed over the teeth of the patient in the area in which surgery is to be performed. The die element 42 is pressed onto the teeth, thus deforming the deformable material 44 and conforming the deformable material 44 to the teeth, thereby attaching the deformable material 44 to the teeth at least by a form fit between the deformable material 44 and the teeth. The die element 42 with the deformable material 44 received therein may be maintained in this position on the patient's teeth for a predetermined period of time, in order to allow the deformable material 44 to harden or cure.

Subsequently, the die element 42 is removed from the teeth of the patient, while the deformable material 44 is held in its position at least by the form fit with the teeth and, in some embodiments, also by an adhesive force between the, preferably hardened or cured, deformable material 44 and the teeth. In this way, the deformable material 44 is released from the die element 42 upon removal of the die element 42 from the teeth.

The deformable material 44 is thus securely held on the teeth of the patient. The surface of the deformable material 44 which faced the die element 42 forms an outer surface of the attached marker member, which is comprised of the deformable material 44 and the marker elements 46, and has the marker elements 46 arranged thereon. These marker elements 46 are detectable by the imaging unit 4 of the navigation system, as is indicated by dashed lines in FIG. 4.

The positioning tool 40 allows for a particularly reliable and precise positioning and attachment of the marker member to the patient's cranial bone, facial bone, tooth or teeth and can thus be particularly advantageously used with the navigation system of the invention.

A set of positioning tools 40 is obtained by providing four positioning tools 40 as shown in FIG. 4, wherein the die elements 42 of the four positioning tools 40 have different shapes and/or sizes from each other. In particular, the set of positioning tools 40 may consist of four positioning tools 40, the die element 42 of each of which is configured, e.g., shaped and sized, for placement over the teeth of a different quadrant of the human or animal jaw.

The foregoing embodiments and their variants have been disclosed for illustrative purposes only, and further variation is wholly possible within the capabilities of the skilled reader. Accordingly, the appended claims are intended to cover all modifications, substitutions, alterations, omissions and additions which one skilled in the art could achieve from the foregoing disclosure, taking into account his own general and specialist kn ledge and expertise.

The invention claimed is:

1. A navigation system for dental and cranio-maxillofacial surgery, comprising:
    a marker member attachable to at least one of a cranial bone, a facial bone, and a tooth or teeth of a patient, wherein the marker member comprises a plurality of marker elements;
    a surgical handpiece;
    an imaging unit which is movably attached to the surgical handpiece, the marker elements being detectable by the imaging unit;
    a sensor and/or detector unit adapted to sense or detect at least an angular position of the imaging unit relative to the surgical handpiece, the imaging unit being rotatably attached to the surgical handpiece.

2. The navigation system according to claim 1, wherein the imaging unit is lockable in a plurality of positions relative to the surgical handpiece.

3. The navigation system according to claim 1, wherein the marker member further comprises a radiopaque material.

4. The navigation system according to claim 1, wherein the marker elements are arranged in a two-dimensional pattern.

5. The navigation system according to claim 1, further comprising a processing unit for processing imaging data of the imaging unit.

6. The navigation system according to claim 1, further comprising a display unit for displaying imaging data of the imaging unit.

7. The navigation system according to claim 6, wherein the display unit is configured to combine the imaging data of the imaging unit with other imaging data and/or treatment planning data.

8. The navigation system according to claim 1, wherein the surgical handpiece is a drill.

9. The navigation system according to claim 1, further comprising a positioning tool, wherein the positioning tool is configured for positioning the marker member on at least one of a patient's cranial bone, facial bone and tooth or teeth, the positioning tool comprising:
    a die element; and
    the marker member, wherein the marker member comprises a deformable material, the deformable material being releasably ably received in the die element, the plurality of marker elements being arranged on a surface of the deformable material which faces the die element.

10. A navigation method for dental and cranio-maxillofacial surgery using the navigation system according to claim 1, the method comprising the steps of:

imaging at least part of the area in which surgery is performed by means of the imaging unit;

determining whether the plurality of marker elements are detected by the imaging unit; and moving the imaging unit relative to the surgical handpiece to a position in which the imaging unit detects the plurality of marker elements, if it is determined that the plurality of marker elements are not detected by the imaging unit.

11. The navigation system according to claim 1, further comprising a set of positioning tools, the set of positioning tools comprising four positioning tools, wherein each positioning tool comprises:

a die element; and the marker member, wherein the marker member comprises a deformable material, the deformable material being releasably received in the die element, the plurality of marker elements being arranged on a surface of the deformable material which faces the die element;

wherein the die elements of the four positioning tools have different shapes from each other.

12. The navigation system according to claim 1, wherein the imaging unit is rotatably attached to the surgical handpiece via an attachment member.

13. The navigation system according to claim 12, wherein the attachment member includes the sensor unit.

14. The navigation system according to claim 1, wherein the imaging unit is arranged to move relative to the handpiece when the marker member is not detected by the imaging unit.

15. The navigation system according to claim 1, wherein the imaging unit is arranged to move relative to the handpiece to maintain visual contact with the marker member during a surgical procedure.

16. The navigation system according to claim 14, wherein the imaging unit includes at least one of a camera unit, a stereoscopic camera unit, and a 3D scanner.

17. The navigation system according to claim 1, wherein the sensor and/or detector unit includes a piezoelectric sensor or detector.

18. The navigation system of claim 1, wherein the sensor and/or detector unit is adapted to sense or detect a least one of a longitudinal and a lateral position of the imaging unit relative to the surgical handpiece.

19. A navigation system for dental and cranio-maxillofacial surgery, comprising:

a marker member attachable to at least one of a cranial bone, a facial bone, and a tooth or teeth of a patient, wherein the marker member comprises a plurality of marker elements arranged to be detectable;

a surgical handpiece;

an imaging unit which is movably attached to the surgical handpiece, the imaging unit adapted to obtain or provide image data of an area of surgery; and a sensor and/or detector unit adapted to sense or detect at least an angular position of the imaging unit relative to the surgical handpiece, the imaging unit being rotatably attached to the surgical handpiece.

20. The navigation system of claim 19, wherein the sensor and/or detector unit is adapted to sense or detect a least one of a longitudinal and a lateral position of the imaging unit relative to the surgical handpiece.

* * * * *